United States Patent [19]

Kilthau et al.

[11] 4,005,187
[45] Jan. 25, 1977

[54] DIAGNOSTIC TEST METHOD

[75] Inventors: Gustave F. Kilthau; Diana R. Loftin, both of Houston, Tex.

[73] Assignee: Data Diagnostic Corporation, Houston, Tex.

[22] Filed: June 3, 1974

[21] Appl. No.: 475,797

[52] U.S. Cl. .............................. 424/1.5; 23/230 B; 23/230.6

[51] Int. Cl.$^2$ .................. G01N 33/00; G01T 1/16; G21H 5/02

[58] Field of Search ............ 424/1; 23/230 B, 230.6

[56] References Cited

UNITED STATES PATENTS

| | | | |
|---|---|---|---|
| 3,666,854 | 5/1972 | Eisentraut | 424/1 |
| 3,776,698 | 12/1973 | Eisentraut | 424/1 X |
| 3,793,445 | 2/1974 | Updike et al. | 424/12 |
| 3,799,740 | 3/1974 | Mincey | 424/1 X |

OTHER PUBLICATIONS

Mitchell et al, Journal of Clinical Endocrinology and Metabolism, vol. 20, Nov, 1960, pp. 1474-1483.

Murphy et al., Journal of Clinical Endocrinology and Metabolism, vol. 24, Feb., 1964, pp. 187-196.

*Primary Examiner*—Benjamin R. Padgett
*Assistant Examiner*—Christine M. Nucker

[57] ABSTRACT

A method of measuring a diagnostically significant component in a fluid test sample in which the desired component is selectively adsorbed by a solid adsorbent formed, in situ, in the sample, the amount of the component then being determined by a suitable technique such as, for example, radioassaying. In a preferred embodiment, the invention is directed to thyroid function testing in which the in situ formed solid adsorbent is used to selectively adsorb the free thyroid hormone in the test serum, the amount of thyroid hormone and/or the unsaturated binding capacity of thyroid hormone binding protein being determined by radioassaying methods employing radioisotope labeled thyroid hormone as a tracer.

52 Claims, No Drawings

DIAGNOSTIC TEST METHOD

BACKGROUND OF THE INVENTION

The present invention relates to a method for determining diagnostically significant component in a given test mixture. More particularly, the present invention relates to a method useful in determining thyroid gland activity.

There are numerous instances in which it is desired to separate and/or determine the amount of a particular component in a test sample containing the desired component and additional materials. Of particular interest in this regard are the testing of biological products derived from animal and plant sources. In one aspect, directed at the testing of such biological products, it may be desired to separate and/or determine a given endogenous component present in the product. For example, numerous procedures and techniques are known for the determination, in human sera of hormones, enzymes, antigens, various protein moieties, vitamins, etc., which can be produced in the body. In still another aspect related to the testing of biological products, it is often times important to ascertain the level of an exogenous material as, for example, in the case of humans, materials such as poisons, narcotics, medications, etc., which are introduced into the body orally or intravenously. While in many cases the diagnostic tests involving both endogenous and exogenous components can be conducted directly on the test fluid without prior isolation or separation of the component, more frequently it is necessary that the diagnostically significant component be, at least partially, separated or isolated from the test mixture.

A prime example of a diagnostic test in which separation of the diagnostically significant component from the sample is necessary is found in the methods employed to test thyroid gland function. Currently, two of the most widely used methods employed in the testing of thyroid gland activity are the tests commonly referred to as the T-3 and T-4 tests. The former measures the unsaturated binding capacity of thyroid hormone binding globulin and other proteins in the body fluid, e.g. blood, while the latter measures the total quantity of the hormone thyroxine within a sample of serum, e.g. blood. The T-4 test measures the level of thyroxine ($C_{15}H_{11}I_4NO_4$), while the T-3 test measures the unsaturated thyroid hormone protein binding capacity for T-4. Both methods employ the use of radioisotope labeled hormones as tracers. In both the T-3 and T-4 methods, the tracer hormone is admixed with a test serum from the body which contains the thyroid hormones thyroxine ($C_{15}H_{11}I_4NO_4$), T-4, and triiodothyronine ($C_{15}H_{12}I_3NO_4$), T-3, and the thyroid hormone binding proteins. By radioassaying either the free or the bound hormone, the amount of endogenous hormone which is bound to the thyroid binding hormone proteins within the serum can then be determined.

The accuracy of the T-3 and T-4 tests depends on the effective separation of the free and bound thyroid hormone in the test procedure. U.S. Pat. No. 3,666,854 and 3,776,698 disclose thyroid hormone test procedures in which the desired separation is accomplished by the use of a solid, particulate, inorganic crystalline material which is added to the test fluid, and on which the free or unbound hormones are selectively adsorbed. The T-3 and T-4 tests set forth in those patents, in general, require a relatively large amount of the particulate solid sorbent. Furthermore, to obtain accurate results relatively close control of the solid particle size is necessary. Moreover, in the case of the T-4 test, in order to ensure adsorption of the unbound or free thyroxine on the particulate solid sorbent, it is generally necessary to have an incubation time of approximately 30 minutes, making the test time consuming. It should further be noted that the above described T-3 and T-4 tests, requiring the addition of a solid particulate sorbent to the test solution, pose greater manipulation problems in the laboratory than procedures involving primarily the use of liquids, which can be accurately and easily metered by commonly available laboratory apparatus.

SUMMARY OF THE INVENTION

It is, therefore, an object of the present invention to provide an improved method for separating and detecting a diagnostically significant component in a given test fluid.

Another object of the present invention is to provide a test method in which a diagnostically significant component is separated from a test fluid sample by adsorption of the component on a solid adsorbent formed, in situ, in the test fluid sample.

Still another object of the present invention is to provide an improved diagnostic test for measuring thyroid gland activity.

A particular object of the present invention is to provide an improved test procedure for measuring the unsaturated binding capacity of thyroid hormone binding protein.

Still another particular object of the present invention is to provide an improved test procedure for measuring the total amount of thyroid hormone within a test fluid sample.

These and other objects of the present invention will become apparent from the description given herein and the appended claims.

The above stated objects are accomplished, in one respect, by a method in which a solid adsorbent is formed, in situ, in a test fluid containing a diagnostically significant component, the solid adsorbent being of a nature so as to selectively adsorb the diagnostically significant component, thereby permitting its isolation an separation, and, if desired, its determination by a suitable assaying technique.

The present invention also provides a method for determining thyroid function in which a test fluid sample, such as blood serum, containing an unknown amount of thyroid hormone and an unknown amount of thyroid hormone binding protein is mixed with a radioisotope labeled thyroid hormone followed by the in situ formation of a solid adsorbent of a nature which selectively adsorbs free thyroid hormone, whether labeled or unlabeled. The solid adsorbent containing the adsorbed thyroid hormone is separated from the resulting test fluid and the amount of free radioisotope labeled hormone on the adsorbent or the amount of bound radioisotope labeled hormone in the resulting solution determined by a radioassaying technique.

The invention further provides a method of measuring thyroid hormone in a fluid test sample wherein the thyroid hormone is liberated from the thyroid hormone binding protein and the liberated hormone separated from the resulting test fluid. The separated free thyroid hormone is then mixed with a known amount of thyroid hormone binding globulin and radioactive isotope labeled thyroid hormone. Following equilibration of the mixture, a solid adsorbent is formed, in situ, the solid adsorbent adsorbing the free thyroid hormone. The solid adsorbent material containing the adsorbed free thyroid hormone is then separated from the remainder of the sample and the amount of free labeled thyroid hormone on the solid adsorbent or the amount of bound labeled thyroid hormone in the resulting solution is determined by a radioassaying technique.

In a further embodiment of the present invention, a fluid test sample containing thyroid hormone and thyroid hormone binding protein are acidified to effect separation of the hormone and the binding protein. Following the acidification, the test sample is admixed with a solid sorbent material which effects selective adsorption of the freed thyroid hormone. The solid sorbent material containing the adsorbed thyroid hormone is then separated from the remainder of the acidified fluid test sample and is admixed with an elution liquid which raises the pH of the mixture to a level sufficient to effect elution of the thyroid hormone from the solid sorbent and prevents re-adsorption of the eluted hormone on the sorbent. The elution mixture is then admixed with thyroid hormone binding globulin and a radioactive isotope labeled thyroid hormone following which a solid adsorbent is formed, in situ, in the elution mixture, the solid adsorbent being of a nature so as to selectively adsorb free thyroid hormone whether labeled or unlabeled. A radioassaying procedure, as described above, is then conducted either on the solid adsorbent material or the remaining liquid.

DESCRIPTION OF THE PREFERRED EMBODIMENT

The present invention employs a unique technique in which a diagnostically significant component present in a fluid test sample is, at least partially, removed from the fluid test sample by forming, in situ, in the fluid test sample, a solid adsorbent of such a nature so as to effect selective adsorption of the diagnostically significant component. Selective adsorption, as used herein, is not intended to mean exclusive adsorption but rather connotes a high binding or adsorbing affinity of the solid adsorbent for the component under consideration. Accordingly, other componens, not of diagnostic importance, may also be bound or adsorbed on the solid adsorbent.

While the present invention can be applied to the measurement of a diagnostically significant component in virtually any type of fluid test sample, the method finds particular application in the biological sciences, and especially in diagnostic tests on fluid test samples derived from mammals, particularly humans, or in fluid test samples containing extracts or derivatives therefrom. The method can be used to separate and assay for an endogenous substance present in such a derived test mixture or for an exogenous substance present in such a derived test sample. In the former case, endogenous substances such as hormones, vitamins, various proteins, etc., can be assayed for in the test sample. In the latter instance, substances such as drugs, poisons, medications, etc., which may have been taken orally or intraveneously or which by some other method have been exogenously introduced into the body or have been merely introduced into the test sample.

The method involves bringing together, in the sample fluid to be tested, at least two solutes which react to form a solid adsorbent in the test sample. While in the usual case the solutes are materials which are added to the fluid test sample during the test procedure, under certain circumstances as, for example, when one of the solutes is already present as a natural or original component in the fluid test sample, it is only necessary to add one additional solute which will then combine or react with the originally present solute to form the solid adsorbent and absorb the diagnostically signficant component from the fluid test sample.

Generally speaking, only two solutes are employed. However, it is within the scope of the present invention to employ any number of solutes, the only requisite being that in some manner they react or combine, in the fluid test sample, to form a solid adsorbent which itself can be a mixture of one or more materials. In the preferred case, the solid adsorbents are formed by the interaction of two, water soluble compounds, one of the solutes comprising an ion or the like which will react with an ion or the like of the other solute to form a solid precipitate. It is also possible to employ a water soluble first solute which can undergo a chemical transformation, as for example, by oxidation, and be converted into a different compound which acts as the solid adsorbent. Thus, for example, in a given solution barium sulfide which is soluble in water can be oxidized using hydrogen peroxide (also soluble in water) or some similar oxidizing agent to form barium oxide and/or sulphate, both of which are relatively water insoluble.

The term "water soluble" as used herein, means a material which, under the test conditions and in the amounts of the aqueous solution employed, is sufficiently soluble such that when solutions of two or more such solutes are brought together, there are sufficient dissolved solutes to form the desired amount of solid adsorbent. Likewise, the term "water insoluble" does not necessarily means a substance which has no water solubility. Rather, the term refers to a substance which, under the test conditions and in the amounts of the aqueous solutions involved, will, at least partially, precipitate out to form the solid adsorbent. It will be readily recognized that the degree of water insolubility of a given adsorbent will depend on such readily ascertainable parameters as concentration, temperture, pH, etc.

While as noted above, one of the solutes which combine to form the solid adsorbent employed in the method of the present invention can be an originally occurring solute in the sense that it is already present as a constituent of the material to be analyzed, more generally, the two or more solutes, preferably in the form of aqueous solutions, are added to the test samples at the time of testing. As employed herein, the term, "aqueous solution" is not intended to mean a solution comprised of a solid dissolved solely in water, but is intended to encompass solutions which may contain, in addition, solvents other than water as, for example, water miscible alcohols, ketones, ethers and other such organic solvents. The solutes can be organic, inorganic-/organic or purely inorganic in nature, and in the preferred case are both inorganic in nature. It will be appreciated that in most and preferred cases, the solutes are ionic in nature, the formation of the solid adsorbent resulting from the combining of one or more soluble cations with one or more soluble anions to form one or more precipitates which act as the solid adsorbent(s) herein.

While as indicated above, a wide variety of solutes varying in chemical makeup can be employed to effect the in situ formation of a solid adsorbent as per the method of the present invention, there are several classes or groups of compounds which have been found to be particularly desirable. One such group consists of the water soluble carboxylic acids and their water soluble salts, water soluble carbonates, water soluble phosphates, water soluble hydroxides, water soluble silicates, water soluble aluminates, water soluble sulphates and mixtures of such compounds. The carboxylic acids and their salts which are useful are the acids or salts of acids which will combine with one of the metal ions of Groups IIa, IIIa, IVa, Ib,IIb, IVb and VIII of the Periodic Table to form, in the test solution, a water insoluble, solid adsorbent.

Specific, non-limiting examples of the above group of compounds include oxalic acid, sodium and ammonium oxalate, sodium-, potassium-, and ammonium carbonate, sodium and ammonium phosphate, phosphoric acid, sodium and ammonium hydroxide, sodium and potassium silicate, sodium aluminate, sodium and ammonium sulphate and the like. In general, in the case of salts, the alkali metal and ammonium salts of the above substances are especially preferred because of their ready availability and water solubility. A particularly desirable solute of the above group comprises the alkali metal carbonates, e.g. sodium carbonate.

A second group of substances from which one of the solutes can be chosen consists of the water soluble salts of the metallic elements of Groups IIa, IIIa, IVa, Ib, IIb, IVb and VIII of the Periodic Table and mixtures thereof. Examples include the water soluble halides, nitrates, nitrites, sulfates, carboxylic acid salts, etc., of the above-named metals. Specific, non-limiting examples include compounds such as magnesium nitrate, magnesium and calcium chloride, barium sulfide, aluminum ammonium sulphate, aluminum fluorsilicate, cupric nitrate, zinc chloride and nitrate, zinc acetate, mecuric lactate, lead nitrate, mecuric nitrate, cadmium nitrate, ferric ammonium oxalate, ferric ammonium citrate, ferric chloride, silver nitrate, copper nitrate, zirconium nitrate, calcium lactate, and the like. An especially preferred group of solutes from this latter group are the water soluble, alkaline earth metal halides such as calcium and magnesium chloride.

It will be readily recognized that when an aqueous solution of one or more of certain of the substances present in the first group mentioned above is mixed with an aqueous solution of one or more of certain of the substances included within the second group of solutes mentioned above, there will be formed a water insoluble precipitate which will act as a solid adsorbent. It should also be observed that in certain cases, it is possible to have the two or more solutes, which react to form the adsorbent, present in the same solution, the precipitation of the solid adsorbent being effected by a change in pH, temperature, etc. Thus, certain solid adsorbents which are soluble in acid solutions will precipitate out upon a raising of the pH.

It is also possible to choose two or more solutes from the second group of solutes noted above which combine to form a water soluble, solid adsorbent. Accordingly, the solid adsorbents herein may be formed by bringing together, in preferably aqueous solution, two or more of the water soluble salts of the metallic elements of Groups IIa, IIIa, IVa, Ib, IIb, IVb and VIII of the Periodic Table which will react to form a generally water insoluble precipitate which will act as the solid adsorbent. Under such circumstances, the solid adsorbent would be formed in accordance with the general equation $M_1X + M_2Y \longrightarrow M_1Y$ (precipitate) $+ M_2$ (cation) $+ X$ (anion) and $M_2$ represent cations of where $M_1$ metals of the above listed Groups and X and Y are anions, respectively. In certain cases it may be possible for the cation $M_2$ to combine with the anion X to form a second precipitate, $M_2X$, which can also act as a solid adsorbent. A prime example of a reaction as per the above equation occurs in the use of aqueous solutions of silver nitrate and calcium chloride which, when combined, will form water insoluble silver chloride, calcium ions and nitrate ions.

The amount of the solid absorbent which must be formed in a given test solution will depend upon several readily ascertainable parameters. Such parameters include the type and amount of the diagnostically significant component, the type and amount of the sample in which the diagnostically significant component is present, the type of solid adsorbent formed, the effect of added, non-solid adsorbent producing ions, etc. For example, with regard to the type of solid adsorbent formed, it will be apparent that if the solid adsorbent is comprised of substance(s) which are of relatively low density but relatively high surface area, less solid adsorbent need be formed than if the material is more dense and has relatively low surface area. Thus, any amount of the solid adsorbent necessary to carry out the desired procedure can easily be formed simply by adding the proper proportions of the solutions containing the solutes in the proper concentrations. It has been found preferable in carrying out diagnostic tests related to thyroid gland activity employing radioassaying methods, and described more fully hereafter, that the amount of solid adsorbent formed should be from about 0.1 to about 20 mg and preferably from about 0.5 to about 10 mg/0.1 ml of the test serum, e.g. blood serum, used. It is to be understood, however, that the above amounts are only preferred and that the amount of solid adsorbent formed can vary over wide limits.

As noted above, the method of the present invention finds broad application, particularly in the area of separation and analysis of diagnostically significant components present in biological materials. Thus, for example, the method could be employed in the study of enzymes. Specifically, if a bacteria capable of producing the enzyme penicillinase and a suitable culture medium are incubated together for a period of time under proper conditions, the enzyme penicillinase will be produced. In such a procedure, following the proper incubation time, a solid adsorbent produced as described above could be formed, in situ, in the medium, the solid adsorbent serving to adsorb the penicillinase in the mixture. Following separation of the solid adsorbent by some suitable means such as centrifugation, any pertinent measurements on the adsorbed penicillinase could be carried out.

MEASUREMENT OF UNSATURATED BINDING CAPACITY OF THYROID HORMONE BINDING GLOBULIN AND OTHER PROTEINS — THE T-3 TEST

This test is designed to measure the free binding sites present in the thyroid hormone binding proteins, particularly thyroid binding globulin (TBG). TBG preferentially binds thyroxine ($T_4$). Accordingly, if triiodothyronine ($T_3$) is added to a mixture containing TBG and bound T-4, the T-3 will not ordinarily displace the T-4 from the TBG but will only bind to the free sites on the TBG. In conducting the test, fixed amounts of sample and control fluids are admixed with like amounts of T-3 labeled with either radioactive $I^{131}$ or $I^{125}$ or, for that matter, any radioactive tracer such as a radioactive isotope of iodine, tritium, nitrogen or carbon. The amount of the tracer hormone added is in excess of the available sites on the TBG available for binding of the T-3. In a short time, the available TBG sites bind as much T-3 as they can. A solid adsorbent is then formed, in situ, in the two test fluids, i.e. the sample and control, the solid adsorbent having high absorbing capacity for free T-3, whether labeled or unlabeled. In a short time after formation of the solid adsorbent, T-3 not bound to TBG is adsorbed by the solid adsorbent. The solid adsorbent is separated from the liquid phase and a radioassay, e.g. scintillation counting, of the labeled T-3 in the liquid phase or the solid adsorbent is conducted.

It is common practice in the T-3 method to express the result as percent uptake by the sample TBG of the added labeled T-3 compared to pooled, normal human serum control TBG uptake, or as percent labeled T-3 uptake by the solid adsorbent of the total amount of labeled T-3 added. Accordingly, the T-3 test serves as a means of estimating the prior saturation of the TBG present in the sample by endogenous T-4 and is, accordingly, a reflection of thyroid gland functioning. It should be observed that while usually, labeled T-3 is employed in the T-3 test, in an analogous procedure, labeled T-4 can likewise be employed. In the latter event, the binding capacity of serum proteins other than TBG is also measured, unless a barbitol buffer is employed which virtually limits binding to TBG.

In the method herein, a measured amount as, for example, 0.05 to 0.5 ml of the test fluid, e.g. blood serum, is admixed with 1 to 10 ml of an aqueous solution containing $I^{125}$ labeled T-3, a first solute, e.g. sodium carbonate, and a suitable buffer which maintains the pH of the solution at from about 8 to about 9.2. The sample is thoroughly mixed after which approximately 1 to 10 ml of an aqueous solution containing a second solute, e.g. calcium chloride, is added. The resulting mixture is then shaken and centrifuged to effect separation of the solid adsorbent, e.g. calcium carbonate.

To carry out the radioassay, the supernatant liquid can be counted in a suitable scintillation counting apparatus or alternately, the solid adsorbent which has been separated by centrifugation can be counted.

In determining the results of the T-3 test, a control sample of pooled serum having a known T-3 value is usually employed, the control sample being treated in the manner described above for the actual test sample. Conveniently, the final radioactivity of the processed control sample can be counted to a given count value and the test samples counted for a time equal to that used to arrive at the count value for the control. Using the number of counts obtained from the test samples, the T-3 values can be obtained from a suitably derived standard curve or mathematically expressed as percent count of sample vs. count of control or as percent count adsorbed by the solid adsorbent vs. the count of the total radioactivity placed in the sample mixture. For the preparation of such a standard curve see, for example, Mitchell, M. L., *The In Vitro Resin Sponge Uptake of Triiodothyronine-$I^{131}$ from Serum in Thyroid Disease and in Pregnancy*, J. Clin Endocrinol 20, 1474 (1960).

ASSAY OF TOTAL SERUM THYROXINE — THE T-4 TEST

This test utilizes the well known "competitive protein binding technique" such as described by Murphy et al, *Determination of Thyroxine Utilizing the Property of Protein Binding*, J. Clin Endocr. Metab. 24, 187 (1964). One method of conducting the T-4 test is to liberate the thyroxine from the thyroid hormone binding protein by well known methods such as precipitation or denaturation. For example, it is well known that organic solvents such as methanol, ethanol, proponol, etc., can be used to precipitate the protein. The free thyroxine is then separated from the precipitated protein, admixed with a solution containing labeled thyroxine and TBG in known amounts. Following equilibration, the solid adsorbent is formed, in situ, the adsorbent selectively adsorbing the free thyroxine. The solid adsorbent is separated from the mixture and the amount of free thyroxine is ascertained by radioassaying either the solid adsorbent containing the free labeled thyroxine or the labeled thyroxine remaining in the supernatant liquid. In the preferred case, one of the solutes is added together with the labeled thyroxine and TBG, the other solute being subsequently added.

In still another and more preferred embodiment of the T-4 test method, a sample, such as a blood sample, containing thyroxine and TBG is acidified to a pH of from about 1 to about 2 to effect separation of the thyroxine from the TBG. The acidified test sample is then admixed with a solid sorbent which adsorbs the free thyroxine. The sorbent containing the freed thyroxine adsorbed thereon is separated from the remainder of the acidified sample, the former being mixed with an alkaline elution liquid which has a pH sufficient to effect desorption of the thyroxine from the solid sorbent and prevent its re-adsorption by that sorbent, the pH generally ranging from about 9 to about 10.5. The alkaline mixture is then mixed with a known amount of labeled thyroxine and TBG and the solid adsorbent is formed, in situ, the solid adsorbent acting to selectively adsorb the free thyroxine whether labeled or unlabeled. Again, either the solid adsorbent containing labeled thyroxine or the supernatant liquid containing labeled thyroxine is radioassayed and the T-4 value obtained from a calibration curve obtained by conducting the above procedure on serum samples having known T-4 values.

In conducting the latter described T-4 test method, from about 0.05 to about 0.5 ml of the test serum is added to a test tube containing from about 2.5 to about 25 ml of a suspension having a pH of about 1.5 to 1.8 and containing about 10 mg of trichloroacetic acid/ml and about 0.75 mg of bentonite or a like solid adsorbent/ml. Following thorough mixing, the mixture is centrifuged and the supernatant liquid discarded. To the bentonite is added from 1 to 10 ml of a buffered solution having a pH of about 9.6 containing $I^{125}$ labeled T-4, sodium carbonate and pooled human serum. The sample is then thoroughly mixed after which approximately 1 to 10 ml of an aqueous solution containing a second solute, e.g., calcium chloride, is added. This results in the formation of the solid adsorbent, e.g. calcium carbonate. The mixture is centrifuged to effect separation of the solid adsorbent from the supernatant liquid and allows counting of either the solid adsorbent or the supernatant liquid to ultimately ascertain the T-4 value.

The solid sorbent added can be any of several substances usually naturally occurring minerals or clays such as bentonite, silica, talc, kaolin, etc. Usually from about 3 to about 10 mg of the solid sorbent is used for each 0.1 ml of test serum.

The first solute is generally added together with the labeled thyroxine, the TBG and the alkaline substance used to bring the mixture to the desired basic pH. Following equilibration (5 minutes or more at ambient temperature), the second solute is usually added to the mixture of the solid sorbent, the alkaline solution, the TBG and the labeled thyroxine.

It is to be pointed out that in the above described method, the alkaline solution used to adjust the pH to the desired elution range can be added alone, as described, or can be added in combination with the labeled thyroxine and TBG, the latter being the preferred method by virtue of convenience.

In still another method for the determination of the total thyroxine in a fluid test sample, a dilution technique may be employed. In this method, the thyroxine is liberated from the thyroid binding protein preferably either by acidification (pH of about 1 to about 3) or alkalinization (pH of about 12 to 14). Once the thyroxine has been freed from he thyroid hormone binding proteins, it is maintained in that state by maintaining the pH acidic or basic enough to prevent recombination of the protein and the thyroxine. A measured amount of labeled thyroxine is then added to the test sample containing the freed thyroxine followed by the formation, in situ, in the total mixture of a solid adsorbent which selectively adsorbs free thyroxine, whether labeled or unlabeled. Following separation, the solid adsorbent containing adsorbed free labeled thyroxine or the labeled thyroxine remaining in solution is then radioassayed. The amount of thyroxine originally present in the test serum can be determined by comparing the dilution effect on the added labeled thyroxine by the endogenous thyroxine in the serum with the similarly obtained dilution effect in control samples of known T-4 content. For example, a graph, based on dilution effect, could be plotted using the values obtained on the known T-4 samples.

The liberation of the thyroxine from the thyroid hormone binding protein can be accomplished by acidification, alkalinization or denaturation of the fluid test sample. In any event, the binding between the thyroxine and the protein is broken, liberating the thyroxine. By maintaining the fluid test sample in the acid, or denatured basic condition, the thyroxine will remain free, i.e. unbound to the protein. Accordingly, separation of the thyroxine from the protein is not necessary and the measurement can be carried out directly in the presence of the protein.

To more fully illustrate the invention, the following non-limiting examples are presented. It is to be understood that the terms, "first solute" and "second solute", used in the examples and otherwise herein in referring to the compounds employed to form the solid adsorbents are not intended to refer to the order of addition of the solutes to the test fluid, but are merely for purposes of description only. Accordingly, a "second solute" could be added to or present in the fluid test sample initially, the solid adsorbent being formed by the subsequent addition of the "first solute."

EXAMPLE 1

This example demonstrates the ability of various in situ formed solid adsorbents to function to selectively adsorb, from a given test mixture, a diagnostically significant component, in this case thyroxine. The general method employed was as follows: Two serum samples identical in all respects but containing different amounts of T-4 were each tagged with the same amount of thyroxine labeled with $I^{125}$. Approximately 0.1 ml of each of the tagged serum samples was placed in separate test tubes and diluted with 2 ml of deionized water. At this point, approximately 0.1 ml of a solution containing one solute was added to the serum sample and the resulting solution mixed. Following this, 0.1 ml of a second solution containing a second solute was added at which point the solutes combined to form the solid adsorbent. The mixtures were centrifuged and the solids which formed, i.e. the solid adsorbents containing the adsorbed T-4, were counted using a scintillation counter. Except as otherwise indicated, the solutions containing the solutes were aqueous solutions of the solutes made up to concentrations of approximately 0.1 molar. Serum Sample 1 contained 14.5 $\mu$gm of $T_4$/100 ml of solution, while Serum Sample 2 contained 9.4 $\mu$gm of $T_4$/100 ml of solution. The table below shows the results obtained.

Table 1

| First Solute | Second Solute | Solid Adsorbent Formed | Serum Sample 1 | Serum Sample 2 |
|---|---|---|---|---|
| | | | Counts × 10-3 | |
| Hydrogen peroxide | Barium sulfide | Barium oxide/sulfate | 6.4 | 5.2 |
| Lead nitrate | Sodium carbonate | Lead carbonate | 44.4 | 40.0 |
| Cupric nitrate | Sodium carbonate | Copper carbonate | 40.8 | 39.6 |
| Cupric nitrate | Barium sulfide | Copper sulfide | 6.0 | 5.2 |
| Cadmium chloride | Sodium carbonate | Cadmium carbonate | 23.6 | 21.2 |
| Zinc chloride | Sodium carbonate | Zinc carbonate | 41.2 | 40.0 |
| Aluminum chloride[1] | Sodium hydroxide | Aluminum hydroxide | 25.2 | 40.0 |
| Zirconium nitrate | Sodium hydroxide[2] | Zirconium hydroxide | 48.0 | 52.0 |
| Cobalt chloride | Sodium hydroxide[2] | Cobalt hydroxide | 11.6 | 14.4 |

[1]Serum Sample mixed in 2 ml of 4% NaOH instead of deionized water
[2]4% Solution As can be seen from the table above, the solid adsorbents which were formed in situ in the fluid test samples acted to selectively adsorb the free T-4 present in the solutions. As can also be observed from the difference in the counts obtained from the two samples containing different amounts of free, unlabeled T-4, the adsorption of the free T-4 on the solid adsorbent is concentration dependent indicating the method provides the basis of an analytical technique to measure thyroid hormones. It should also be observed, as shown in the example employing barium sulfide and hydrogen peroxide, that the solid adsorbent can be formed by a chemical reaction between one solute (hydrogen peroxide) which acts, in this case via oxidation, to convert a second solute (barium sulfide) into an insoluble material.

EXAMPLE 2

In this example, the T-3 test, i.e. the test for unsaturated binding capacity of the thyroid hormone binding proteins was conducted using triiodothyronine labeled with $I^{125}$. Into separate test tubes were placed 0.1 ml of a control serum having a known T-3 value of 30% and several test sera of unknown T-3 values. The test samples were each run in duplicate. Two control samples were also used; however, one control sample was treated as an unknown. To each of the samples was added 2 ml of a buffered aqueous solution containing 0.05 $\mu$Ci $I^{125}$ labeled T-3/ml, 2.14 mg sodium carbonate/ml and 0.002 ml of pooled human serum/ml. The added solution had a pH of approximately 8.5. The samples were thoroughly mixed following which 2 ml of an aqueous solution containing 36 mg of calcium chloride/ml was added. The resulting samples were thoroughly mixed and centrifuged for 5 minutes to separate the solid adsorbent (calcium carbonate) which formed. Following centrifugation, the supernatant liquid was counted using a scintillation counter. One control sample was counted to 10,000 counts while the unknown samples plus the other control sample were counted for a period equal to the time for achieving the 10,000 counts on the control. T-3 values for the control sample and the unknown samples were then obtained from a calibration curve. The table below shows the results:

Table 2

| Sample | T-3 Value (%) |
|---|---|
| Control (treated as unknown) | 30.5 |
|  | 34.9 |
| 1 | 34.4 |
|  | 31.5 |
| 2 | 31.5 |
|  | 38.7 |
| 3 | 38.3 |
|  | 29.0 |
| 4 | 29.5 |
|  | 44.7 |
| 5 | 44.2 |
|  | 29.0 |
| 6 | 29.5 |
|  | 31.5 |
| 7 | 31.9 |
|  | 45.1 |
| 8 | 44.7 |
|  | 29.5 |
| 9 | 29.5 |
|  | 32.4 |
| 10 | 31.5 |

As can be seen from the above results, the T-3 method herein yields highly accurate and reproducible results.

To further demonstrate the reproducibility of the method, the above described T-3 method was carried out on six separate samples of a human serum. The T-3 values obtained for the six different runs are shown below:

| Run No. | T-3 Value (%) |
|---|---|
| 1 | 28.0 |
| 2 | 28.0 |
| 3 | 27.0 |
| 4 | 27.0 |
| 5 | 27.5 |

-continued

| Run No. | T-3 Value (%) |
|---|---|
| 6 | 27.0 |

EXAMPLE 3

In this example, the method of the present invention was used to obtain T-4 values for various samples. The general method was as follows: Into a test tube was placed 5 ml of an aqueous suspension containing 10 mg of trichloroacetic acid/ml and 0.75 mg/ml of bentonite, the solution having a pH of about 1.6. 0.1 ml of the test serum was then added. The contents were thoroughly mixed and allowed to stand for several minutes, following which they were centrifuged for 5 minutes. The supernatant liquid was discarded. There was then added 2 ml of a solution having the following composition: T-4 labeled with $I^{125} \sim 0.05$ $\mu$Ci/ml, sodium carbonate 1.158 mg/ml, pooled human serum 0.015 ml/ml. The solutions were buffered with a barbital buffer to a pH of from 9.0 to 10.2. The resulting sample was thoroughly mixed and allowed to stand at room temperature for 10 minutes. There was than added 2 ml of a solution containing 36 mg of calcium chloride/ml. The resulting mixture was mixed and centrifuged for 5 minutes. Using a scintillation counter, both the supernatant liquid and the solid were counted, and the count values used to determine the T-4 value. The table below shows the results obtained on a series of samples run as per the above method. In most cases the runs were made in duplicate.

Table 3

| Sample | Assigned T-4 Value $\mu$gm % | Solid Adsorbent T-4 Value $\mu$gm % | Supernatant Liquid T-4 Value $\mu$gm % |
|---|---|---|---|
| 1 | 3.5 | 4.0 | 4.2 |
|  | 3.5 | 3.5 | 4.2 |
| 2 | 9.4 | 9.3 | 9.0 |
|  | 9.4 | 9.3 | 9.3 |
| 3 | 14.7 | 15.0 | 15.4 |
|  | 14.7 | 15.3 | 15.1 |
| 4 | 9.2 | 8.8 | 8.6 |
|  | 9.2 | 9.5 | 9.0 |
| 5 | 15.6 | 15.6 |  |
|  | 15.6 |  | 16.2 |
| 6 |  | 10.6 | 10.8 |
|  |  | 10.3 | 10.4 |
| 7 |  | 3.2 | 3.2 |
|  |  | 4.5 | 4.3 |
| 8 |  | 9.5 | 9.7 |
|  |  | 10.0 | 9.3 |
| 9 |  | 14.3 | 14.4 |
|  |  | 14.8 | 14.8 |

As can be seen from the above results, the T-4 method of the present invention is highly reproducible and, as evidenced by sample 1–5, quite accurate in determining T-4 values.

EXAMPLE 4

This example demonstrates the use of the method of the present invention in a T-4 test based on dilution of labeled T-4 added to a test sample. Two T-4 controls having assigned or known T-4 values were employed. Serum Sample 1 contained 9.2 $\mu$gm % T-4, while Serum Sample 2 contained 15.6 $\mu$gm % T-4. 0.1 ml of the serum samples was placed in separate test tubes. To each was added 1 ml of a phosphoric acid solution of calcium chloride containing 36 mg of calcium chloride/ml and having a pH of 1.5. Following mixing, there was added to each tube 0.1 ml of a solution having the following composition: 5 ml of barbital buffer of ionic strength, 0.075, 10 μl of 10% albumin and 5 μCi of $I^{125}$ labeled T-4. The solution had a pH of approximately 8.6. The resulting solution was mixed and there was then added 2.5 ml of a barbital buffer of ionic strength, 0.075, having a pH of 8.6. Upon addition of the barbital buffer and mixing, there was formed a solid adsorbent comprised of calcium phosphate, the final mixture having a pH of approximately 5. The serum samples were centrifuged and the solid adsorbent in each case counted using a scintillation counter. The results are shown below:

|  | Run No. 1 Counts | Run No. 2 Counts |
| --- | --- | --- |
| Serum Sample 1 | 10,000 | 10,000 |
| Serum Sample 2 | 7,750 | 7,730 |

As can be seen, a differential counting rate is obtained between the two T-4 serum samples having different amounts of T-4 therein. Thus, the above described dilution technique provides the basis for a measurement of total serum T-4 without the normal procedure of separating the T-4 from the T-4 binding proteins. The example also demonstrates that the amount of solid adsorbent formed can be controlled. For example, it was only after the pH of the phosphoric acid solution of $CaCl_2$ was raised that the calcium phosphate precipitated. The example further demonstrates that the solutes can be present in the same solution, the formation of the solid adsorbent being brought on by a change of pH sufficient to effect precipitation.

EXAMPLE 5

This example demonstrates a method useful in determining T-4 values in which the T-4 is liberated from the binding protein by means other than acidizing followed by binding of the liberated T-4 on a solid sorbent as in Example 3. 0.4 ml of the serum sample was mixed with 1 ml of methyl alcohol, shaken and centrifuged. 0.3 ml of the supernatant liquid was separated from the precipitated protein and was evaporated under air. To the dried extract was added 2 ml of an aqueous sodium carbonate solution containing $I^{125}$ labeled T-4 described in Example 3 above. There was also added 0.01 ml of an albumin solution known to be free of T-4. The solution was mixed and allowed to stand at room temperature for 10 minutes after which there was added 2 ml of a calcium chloride solution containing 36 mg of calcium chloride/ml. The mixture was shaken and centrifuged to separate out the calcium carbonate, solid adsorbent which formed. Following centrifugation, the solid adsorbent was counted using a scintillation counter. The above method was conducted on two known value pooled human serum samples, Serum Sample 1 containing 9.4 μgm % T-4, Serum Sample 2 containing 14.0 μgm % T-4. The results are shown below:

|  | Counts |
| --- | --- |
| Serum Sample 1 | 10,000 |
| Serum Sample 2 | 11,600 |

The above results demonstrate that a method for determining T-4 in human serum can be employed without the necessity for separating the T-4 from the T-4 binding protein by the use of acidizing and adsorption on an added solid sorbent.

EXAMPLE 6

Specific examples of various solutes which have been employed to form solid adsorbents capable of selectively adsorbing thyroid hormone from serum samples are given below. In all cases the solutes were in aqueous solutions and were generally present in amounts such that from 0.5 to 10 mg of solid adsorbent were formed for each 0.1 ml of serum sample used.

| Solute 1 | Solute 2 | Solid Adsorbent Formed |
| --- | --- | --- |
| Sodium hydroxide | Magnesium chloride | Magnesium hydroxide |
| Potassium phosphate | Calcium chloride | Calcium phosphate |
| Sodium hydroxide | Calcium chloride | Calcium hydroxide |
| Ammonium oxalate | Calcium chloride | Calcium oxalate |
| Calcium chloride | Silver nitrate | Silver chloride |
| Sodium silicate | Magnesium chloride | Magnesium silicate |
| Oxalic acid | Zinc sulfate | Zinc oxalate |
| Oxalic acid | Cobalt chloride | Cobalt oxalate |
| Oxalic acid | Copper nitrate | Copper oxalate |
| Sodium aluminate | Calcium chloride | Calcium aluminate |

As can be seen from the above, numerous combinations of solutes can be employed to form various solid adsorbents. It should be noted that in this example, a solid adsorbent was formed using two water soluble salts of metals listed above as forming a desirable group of second solutes. Thus, for example, silver nitrate, a solute containing a metal from Group Ib combines with calcium chloride, a solute of a metal from Group IIa to form insoluble silver chloride.

It will be apparent to one skilled in the art that numerous variations and modifications of the method described herein can be employed. In particular, it will be apparent that numerous different solutes can be employed to form, in situ, in the test solution, numerous solid adsorbents. Accordingly, it is intended that the scope of the invention be limited only by the appended claims.

We claim:

1. A method of isolating a diagnostically significant component in a test fluid mixture comprising contacting at least 2 solutes in said test fluid mixture, which solutes react to form in situ a solid absorbent, said solid absorbent formed of material other than said diagnostically significant component and being of a nature so as to selectively adsorb at least a portion of said diagnostically significant component.

2. The method of claim 1 further including the step of separating said solid adsorbent and the adsorbed portion of said diagnostically significant component from the resulting test fluid mixture of claim 1.

3. The method of claim 2 including the step of assaying the separated solid adsorbent and said adsorbed portion of said diagnostically significant component to determine the amount of said diagnostically significant component present in said test fluid mixture.

4. The method of claim 2 including the step of assaying said resulting test fluid mixture from claim 2 to determine the amount of said diagnostically significant component present in said test fluid mixture.

5. The method of claim 1 wherein the contacting step to effect the in situ formation of said solid adsorbent is accomplished by the addition to said test fluid mixture of a solution containing a first solute which reacts in said test fluid mixture with a second solute originally present in said test fluid mixture to form said solid adsorbent.

6. The method of claim 1 wherein the contacting step to effect the in situ formation of said solid adsorbent is accomplished by adding to said test fluid mixture a first solution containing a first solute and a second solution containing a second solute, said first and second solutes reacting in said test fluid mixture to form said solid adsorbent.

7. The method of claim 5 wherein said first solute comprises a water soluble inorganic compound.

8. The method of claim 7 wherein said second solute comprises a water soluble inorganic compound.

9. The method of claim 6 wherein said first and second solutes comprise water soluble inorganic compounds.

10. The method of claim 1 wherein said diagnostically significant component comprises a biologically produced endogenous component.

11. The method of claim 1 wherein said test fluid mixture contains an endogenous biological product and said diagnostically significant component comprises an exogenous material present in said biological product.

12. In a method for determining thyroid function wherein a measured amount of radioisotope labeled thyroid hormone is added to a test fluid containing an unknown amount of said thyroid hormone and an unknown amount of thyroid hormone binding protein to determine the level of binding capacity of said thyroid hormone binding protein by radioassaying of either said free labeled hormone or said labeled hormone which binds to said thyroid hormone binding protein, the improvement comprising:
 1. contacting at least two solutes in said test fluid containing said measured amount of said radioactive labeled thyroid hormone, which solutes react to form in situ a solid adsorbent, said solid adsorbent formed of material other than said thyroid hormone or said thyroid hormone binding protein and being of a nature so as to selectively adsorb free thyroid hormone, and
 2. separating said solid adsorbent containing the adsorbed thyroid hormone from the resulting test fluid prior to said radioassaying.

13. The method of claim 12 wherein the contacting step to effect the in situ formation of said solid adsorbent is accomplished by adding to said test fluid a first solution containing a first solute and a second solution containing a second solute, said first and second solutes reacting in said test fluid to form said solid adsorbent.

14. The method of claim 13 wherein said first solute and said second solute comprise water soluble inorganic compounds.

15. The method of claim 13 wherein said first solute is a water soluble substance selected from the class consisting of carboxylic acids, salts of carboxylic acids, carbonates, phosphates, hydroxides, silicates, aluminates, sulphates, and mixtures thereof and said second solute is selected from the class consisting of water soluble salts of the metallic elements of Groups IIa, IIIa, IVa, Ib, IIb, IVb and VIII of the Periodic Table and mixtures thereof.

16. The method of claim 13 wherein said first solute comprises a water soluble salt of a metallic element of Groups IIa, IIIa, IVa, Ib, IIb, IVb and VIII of the Periodic Table and said second solute comprises a water soluble salt of a metallic element of Groups IIa, IIIa, IVa, Ib, IIb, IVb and VIII of the Periodic Table, the anion of one of said solutes reacting with the cation of the other of said solutes to form said solid adsorbent.

17. The method of claim 13 wherein said first solute comprises an alkali metal carbonate.

18. The method of claim 17 wherein said alkali metal carbonate comprises sodium carbonate.

19. The method of claim 13 wherein said second solute comprises an alkaline earth metal chloride.

20. The method of claim 19 wherein said alkaline earth metal chloride comprises calcium chloride.

21. The method of claim 12 wherein said radioassaying is accomplished by scintillation counting.

22. A method of determining the amount of thyroid hormone binding capacity in a test fluid containing an unknown amount of said thyroid hormone and an unknown amount of thyroid hormone binding protein comprising:
 1. adding to said test fluid a measured amount of radioisotope labeled thyroid hormone,
 2. contacting at least two solutes in said test fluid containing said measured amount of said radioactive labeled thyroid hormone, which solutes react to form in situ a solid adsorbent, said solid adsorbent formed of material other than said thyroid hormone or said thyroid hormone binding protein and being of a nature so as to selectively adsorb free thyroid hormone,
 3. separating said solid adsorbent containing the adsorbed thyroid hormone from the resulting test fluid,
 4. radioassaying either the radioisotope labeled hormone on said solid adsorbent or said bound radioisotope labeled hormone in said resulting solution.

23. The method of claim 22 wherein the contacting step to effect the in situ formation of said solid adsorbent is accomplished by adding to said test fluid a first solution containing a first solute and a second solution containing a second solute, said first and second solutes reacting in said test fluid to form said solid adsorbent.

24. The method of claim 23 wherein said first solute and said second solute comprise water soluble inorganic compounds.

25. The method of claim 23 wherein said first solute is a water soluble substance selected from the class consisting of carboxylic acids, salts of carboxylic acids, carbonates, phosphates, hydroxides, silicates, aluminates, sulphates, and mixtures thereof and said second solute is selected from the class consisting of water soluble salts of the metallic element of Groups IIa, IIIa, IVa, Ib, IIb, IVb and VIII of the Periodic Table and mixtures thereof.

26. The method of claim 23 wherein said first solute comprises a water soluble salt of a metallic element of Groups IIa, IIIa, IVa, Ib, IIb, IVb and VIII of the Periodic Table and said second solute comprises a water soluble salt of a metallic element of Groups IIa, IIIa, IVa, Ib, IIb, IVb and VIII of the Periodic Table, the anion of one of said solutes reacting with the cation of the other of said solutes to form said solid adsorbent.

27. The method of claim 23 wherein said first solute comprises sodium carbonate.

28. The method of claim 23 wherein said first solute comprises potassium phosphate.

29. The method of claim 23 wherein said second solute comprises calcium chloride.

30. The method of claim 22 wherein said radioassaying is accomplished by scintillation counting.

31. A method of isolating thyroid hormone in a test fluid containing said thyroid hormone and thyroid hormone binding protein comprising:
1. admixing sufficient acid or base with said test sample to free said thyroid hormone from said thyroid hormone binding protein, and
2. contacting at least two solutes in said test fluid containing said acid or said base, which solutes react to form in situ a solid adsorbent, said solid adsorbent formed of material other than said thyroid hormone or said thyroid hormone binding protein and being of a nature so as to selectively adsorb free thyroid hormone.

32. The method of claim 31 further including separating said solid adsorbent containing the adsorbed free thyroid hormone from the resulting mixture of step 2.

33. The method of claim 32 wherein said test sample is admixed with acid, the amount of acid added being sufficient so as to result in a pH range of from about 1 to about 4.

34. The method of claim 32 wherein said test sample is admixed with base, the amount of said base added being sufficient so as to result in a pH range of from about 12 to about 14.

35. The method of claim 32 wherein the contacting step to effect the in situ formation of said solid adsorbent is accomplished by adding to said test fluid a first solution containing a first solute and a second solution containing a second solute, said first and second solutes reacting in said test fluid to form said solid adsorbent.

36. The method of claim 35 wherein said first solute and said second solute comprise water soluble inorganic compounds.

37. The method of claim 35 wherein said first solute is a water soluble substance selected from the class consisting of carboxylic acids, salts of carboxylic acids, carbonates, phosphates, hydroxides, silicates, aluminates, sulphates and mixtures thereof and said second solute is selected from the class consisting of water soluble salts of the metallic elements of Groups IIa, IIIa, IVa, Ib, IIb, IVb and VIII of the Periodic Table and mixtures thereof.

38. A method of measuring thyroid hormone in a fluid test sample containing said thyroid hormone and thyroid hormone binding protein comprising:
1. acidifying said fluid test sample to effect separation of said thyroid hormone from said thyroid hormone binding protein,
2. admixing said acidified fluid test sample with a solid sorbent material to effect selective separation of the free thyroid hormone,
3. separating said solid sorbent material containing the adsorbed thyroid hormone from the remainder of said acidified fluid test sample,
4. admixing said solid sorbent material containing said thyroid hormone with an elution liquid to form an elution mixture having a pH sufficiently high enough to effect elution of said thyroid hormone from said solid sorbent,
5. admixing said elution mixture with thyroid hormone binding globulin and a radioactive isotope labeled thyroid hormone,
6. contacting at least two solutes in said elution mixture containing said thyroid binding globulin and said radioactive isotope labeled thyroid hormone, which solutes react to form in situ a solid adsorbent, said adsorbent formed of material other than said thyroid binding globulin or said thyroid hormone and being of a nature so as to selectively adsorb free thyroid hormone, and
7. radioassaying either said labeled thyroid hormone adsorbed by said solid adsorbent or the remaining labeled thyroid hormone in said elution mixture.

39. The method of claim 38 wherein said solid sorbent material comprises bentonite.

40. The method of claim 38 wherein said acidifying is sufficient to adjust the pH of said test fluid to a range of from about 1 to about 3.

41. The method of claim 38 wherein said pH sufficient to effect elution is from about 8.5 to about 11.

42. The method of claim 38 wherein the contacting step to effect the in situ formation of said solid adsorbent is accomplished by adding to said test fluid a first solution containing a first solute and a second solution containing a second solute, said first and second solutes reacting in said test fluid to form said solid adsorbent.

43. The method of claim 42 wherein said first solute and said second solute comprise water soluble inorganic compounds.

44. The method of claim 42 wherein said first solute is a water soluble substance selected from the class consisting of carboxylic acids, salts of carboxylic acids, carbonates, phosphates, hydroxides, silicates, aluminates, sulphates, and mixtures thereof and said second solute is selected from the class consisting of water soluble salts of the metallic elements of Groups IIa, IIIa, IVa, Ib, IIb, IVb and VIII of the Periodic Table and mixtures thereof.

45. The method of claim 43 wherein said first solute comprises an alkali metal carbonate.

46. The method of claim 45 wherein said first solute comprises sodium carbonate.

47. The method of claim 43 wherein said second solute comprises an alkaline earth metal chloride.

48. The method of claim 44 wherein said second solute comprises calcium chloride.

49. The method of claim 42 wherein said first solution containing said first solute is added to said fluid test sample with said elution liquid.

50. The method of claim 49 wherein said second solution containing said second solute is added to said elution mixture following addition of said thyroid hormone binding globulin and said labeled thyroid hormone.

51. A method of measuring thyroxine in a fluid test sample containing thyroxine and thyroid hormone binding protein comprising:
1. liberating said thyroxine from said thyroid hormone binding protein,
2. separating the thyroxine from the resulting fluid test sample of step 1,
3. admixing the thyroxine from step 2 with a fluid containing thyroid hormone binding globulin and radioactive isotope labeled thyroxine,
4. equilibrating the resultant mixture from step 3,
5. contacting at least two solutes in the mixture from step 4, which soluter react to form in situ a solid adsorbent, said solid adsorbent formed of material other than said thyroid hormone binding globulin or said thyroxine and being of a nature so as to selectively adsorb free thyroxine, 6. separating said solid adsorbent material from the resulting mixture of step 5, and
7. radioassaying either the free labeled thyroxine on said solid adsorbent or said labeled thyroxine remaining in said resulting solution from step 6.

52. A tracer dilution method of measuring thyroxine in a fluid test sample containing thyroxine and thyroid hormone binding protein comprising:

1. liberating said thyroxine from said thyroid hormone binding protein,
2. admixing a measured amount of radioisotope labeled thyroxine with the test fluid sample of step 1 containing the free thyroxine,
3. contacting at least two solutes in the mixture from step 2, which solutes react to form in situ a solid adsorbent, said adsorbent formed of material other than said thyroxine and being of a nature so as to selectively adsorb free thyroxine,
4. separating said solid adsorbent containing the adsorbed free thyroxine from the resulting mixture of step 3, and
5. radioassaying either said labeled thyroxine adsorbed by said solid adsorbent or said labeled thyroxine remaining in solution.

* * * * *

UNITED STATES PATENT OFFICE
CERTIFICATE OF CORRECTION

Patent No. 4,005,187            Dated January 25, 1977

Inventor(s) Gustave F. Kilthau; Diana R. Loftin

It is certified that error appears in the above-identified patent and that said Letters Patent are hereby corrected as shown below:

In Column 1, line 66, insert after the word "unbound" the word --thyroid--.

Signed and Sealed this second Day of August 1977

[SEAL]

Attest:

RUTH C. MASON
*Attesting Officer*

C. MARSHALL DANN
*Commissioner of Patents and Trademarks*